Figure 1:
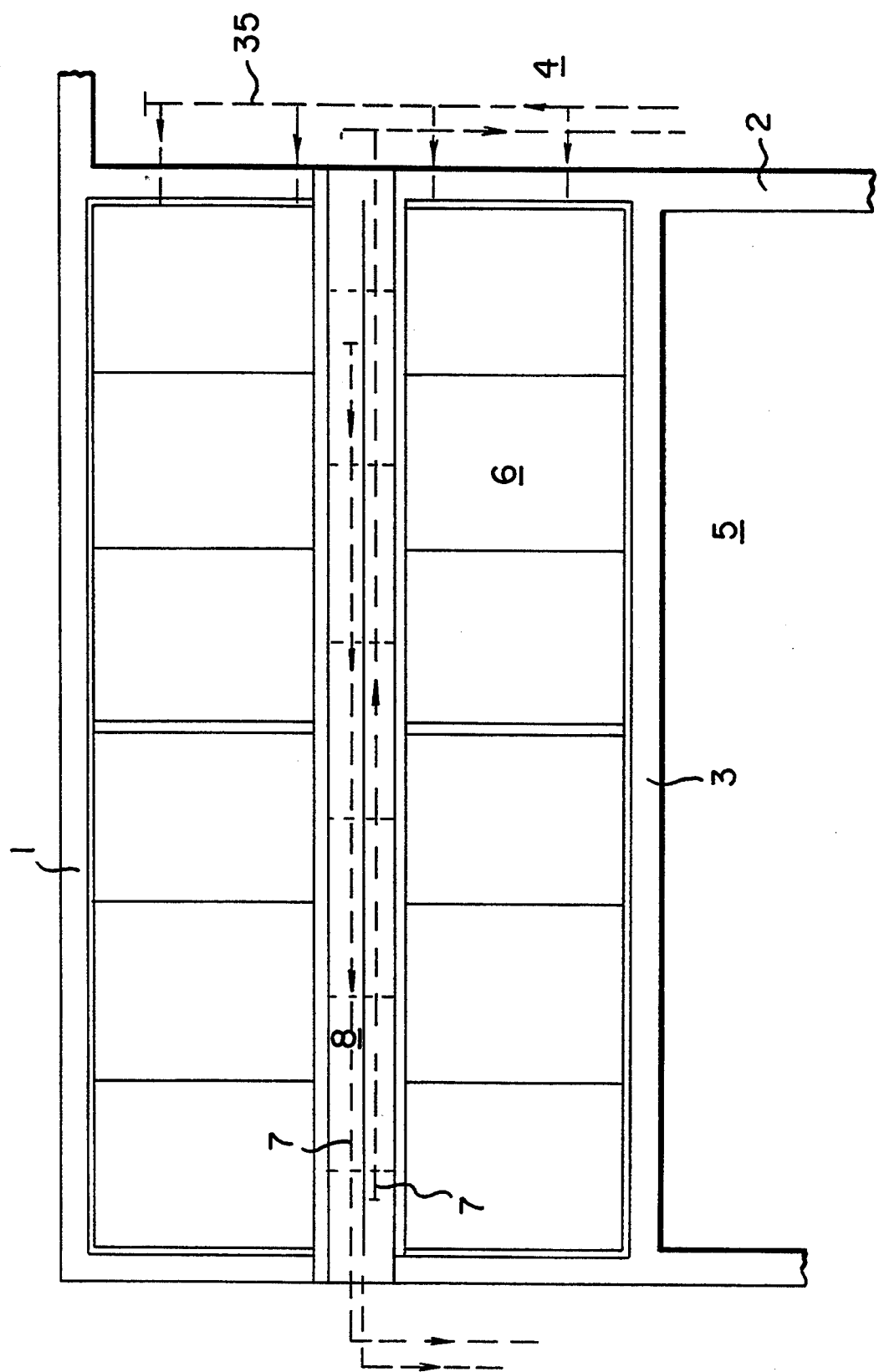

United States Patent [19]
Zumbragel et al.

[11] Patent Number: 5,338,445
[45] Date of Patent: Aug. 16, 1994

[54] MODULE FOR A REACTOR FOR ANAEROBIC WASTE WATER TREATMENT

[75] Inventors: Michael Zumbragel; Volker Bach, both of Aarbergen, Fed. Rep. of Germany

[73] Assignee: Passavant-Werke AG, Fed. Rep. of Germany

[21] Appl. No.: 7,134

[22] Filed: Jan. 21, 1993

[30] Foreign Application Priority Data

Jan. 24, 1992 [DE] Fed. Rep. of Germany ....... 4201864

[51] Int. Cl.⁵ .............................................. C02F 3/28
[52] U.S. Cl. .................... 210/150; 210/188; 210/218; 210/539; 210/603
[58] Field of Search ............... 210/188, 218, 150, 151, 210/522, 538, 539, 540, 603; 55/185, 186, 187, 188

[56] References Cited

U.S. PATENT DOCUMENTS

| | | | |
|---|---|---|---|
| 3,247,650 | 4/1966 | Kornbickle | 35/185 |
| 4,157,958 | 6/1979 | Chow | 210/603 |
| 4,166,791 | 9/1979 | Marvin | 210/188 |
| 4,253,956 | 3/1981 | Pette | 210/788 |
| 4,391,704 | 7/1983 | Anderson | 210/188 |
| 4,622,147 | 11/1986 | Vellinga | 210/539 |
| 4,758,339 | 7/1988 | Vellinga | 210/188 |

FOREIGN PATENT DOCUMENTS 3326879 2/1985 Fed. Rep. of Germany.
3904326 8/1990 Fed. Rep. of Germany.
59-26199 2/1984 Japan.

OTHER PUBLICATIONS

Passavant brochure, 1989.

*Primary Examiner*—Christopher Upton
*Attorney, Agent, or Firm*—Larson and Taylor

[57] ABSTRACT

A module for a UASB (upflow anaerobic sludge blanket) reactor for anaerobic waste water treatment comprises an overflow threshold for the treated waste water that determines the water level in the module. Several immersed collection domes are provided for the digester gas which are staggered over the entire module cross-section and possess a drain into a collection pipe and an upper evacuation line for the waste air collecting above the water level. All walls, covers and installation parts of the module are made of plastic, if necessary reinforced with steel profiles, and are welded to each other. Also, all drains end at a narrow side of the module where they are connected in a gas-tight manner with discharge ducts which have been installed there along several modules and which may be closed off in sections.

9 Claims, 5 Drawing Sheets

MODULE FOR A REACTOR FOR ANAEROBIC WASTE WATER TREATMENT

The invention relates to a module for an upflow anaerobic sludge blanket (UASB) reactor for anaerobic waste water treatment.

During anaerobic waste water treatment, the organic waste water components are broken down into the final products methane ($CH_4$) and carbon dioxide ($CO_2$). Of these, part is incorporated into the cell substance of the microorganisms and must be removed as excess sludge at a later time.

The methane-containing digester gas rising in the reactor must be collected and removed. Because of its high thermal value it is used to generate electricity, power, or heat.

The collection system consists of several layers of completely flooded domes which are arranged on top of each other. Sludge particles which possibly have been pulled along upwards settle on the external dome surfaces and drop back into the reactor. Based on the separation of the digester gas phase and water phase from the "biological sludge" phase, this core part of the reactor is called the "three-phase separation system".

This separation system is manufactured in the form of modules with a rectangular external shape. The modules consist of various materials, whereby the corrosive atmosphere and sealing conditions present here were considered in the selection of materials (Brochure "WSI 92/89 Anaerobe Abwasserreinigung BIOPAQ" of Passavant-Werke AG). The use of the different materials with varying temperature gradients and the incorporation of wood as a support structure have the result that leaks and odor emissions occur. The coupling elements of the components are not corrosion-resistant.

Digester gas, waste air, and treated waste water are removed below the bottom edge of the modules below the water level. As a result, the reactor must be drained at least partially if repair work becomes necessary. This results in down times which are longer than necessary.

The task of eliminating this problem is solved according to the invention in that all walls, covers and installation parts of the module are made of plastic, if necessary reinforced with steel profiles, and are welded to each other; and that all drains end at a narrow side of the module where they are connected in a gas-tight manner with discharge ducts which have been installed there along several modules and which may be closed off by sections. This new construction eliminates any coupling elements. All welding points of the steel profile reinforcements are coated with plastic so as to be corrosion-resistant. All surfaces contacting corrosive media are made of a corrosion-resistant material. The module cover consists of the same material, so that leaks due to different thermal expansion are prevented. The digester gas, waste gas, and treated waste water are now drained through a separate discharge duct which is located alongside the modules and is completely separated from the module interior. Because of this, the reactor no longer must be drained for repair work in the duct. All conduit pipes installed in the duct are readily accessible and their division into lockable sections makes repair and maintenance work easy.

It is advantageous that each module be equipped with a projecting compartment for the collection of digester gas which extends along its entire depth. On top of this compartment is located the discharge duct in which the conduit pipes are installed essentially next to each other and thus easily accessible.

Figure 2:
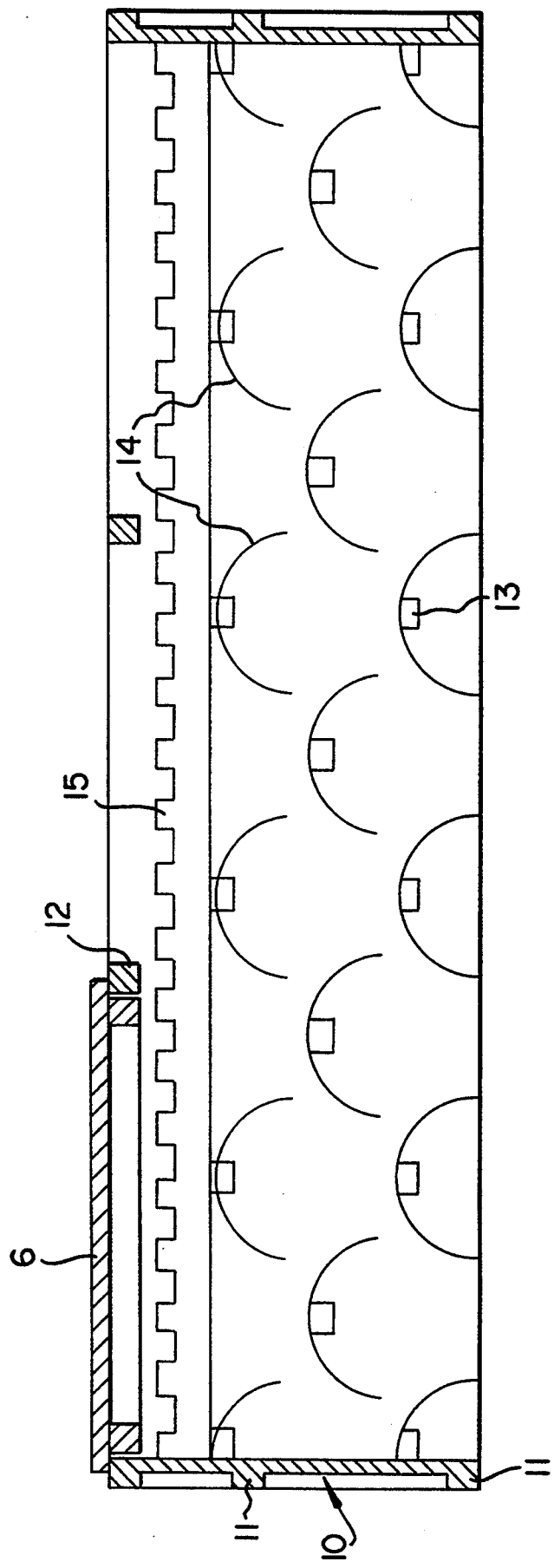
Figure 3:
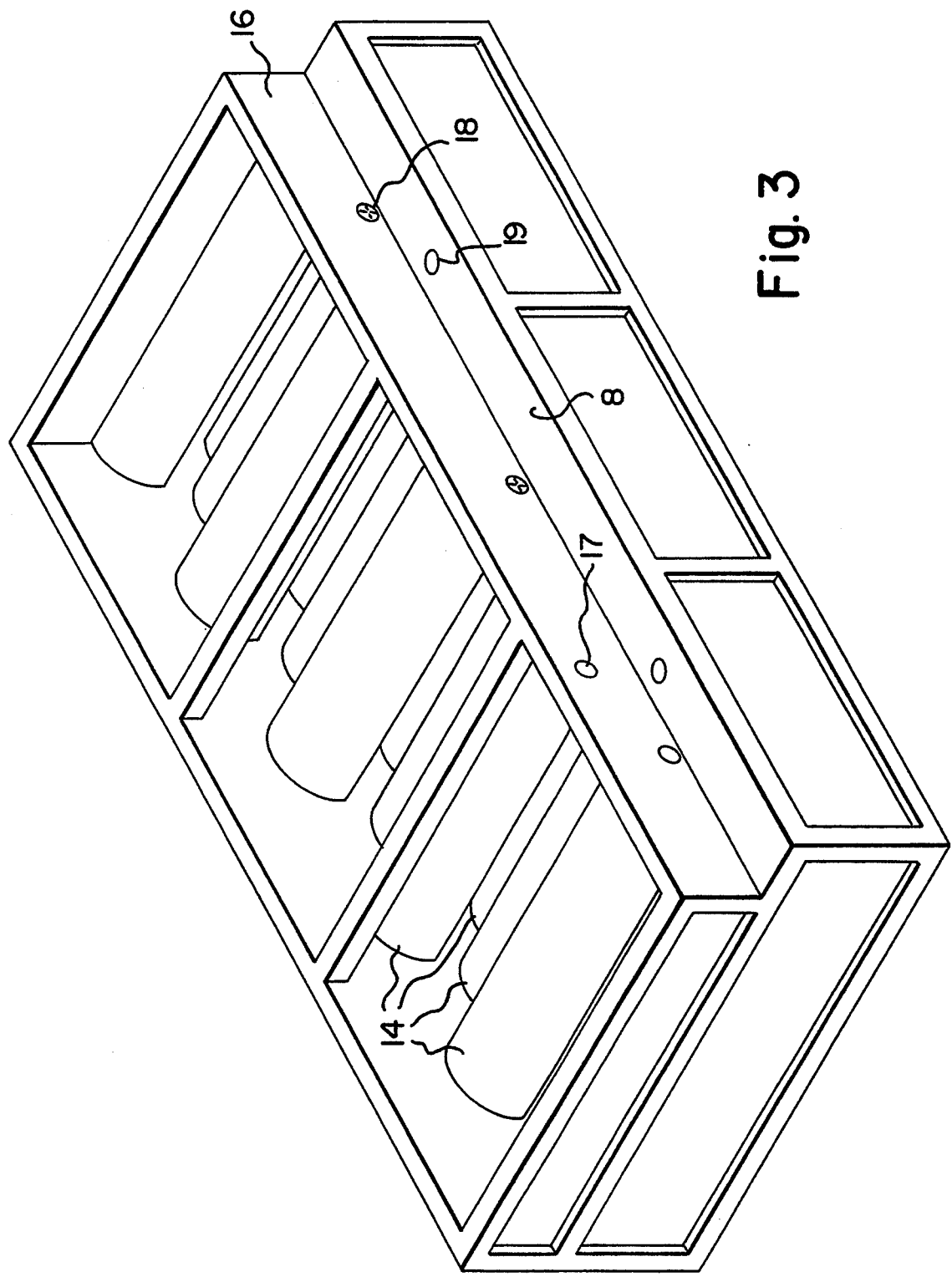
Figure 4:
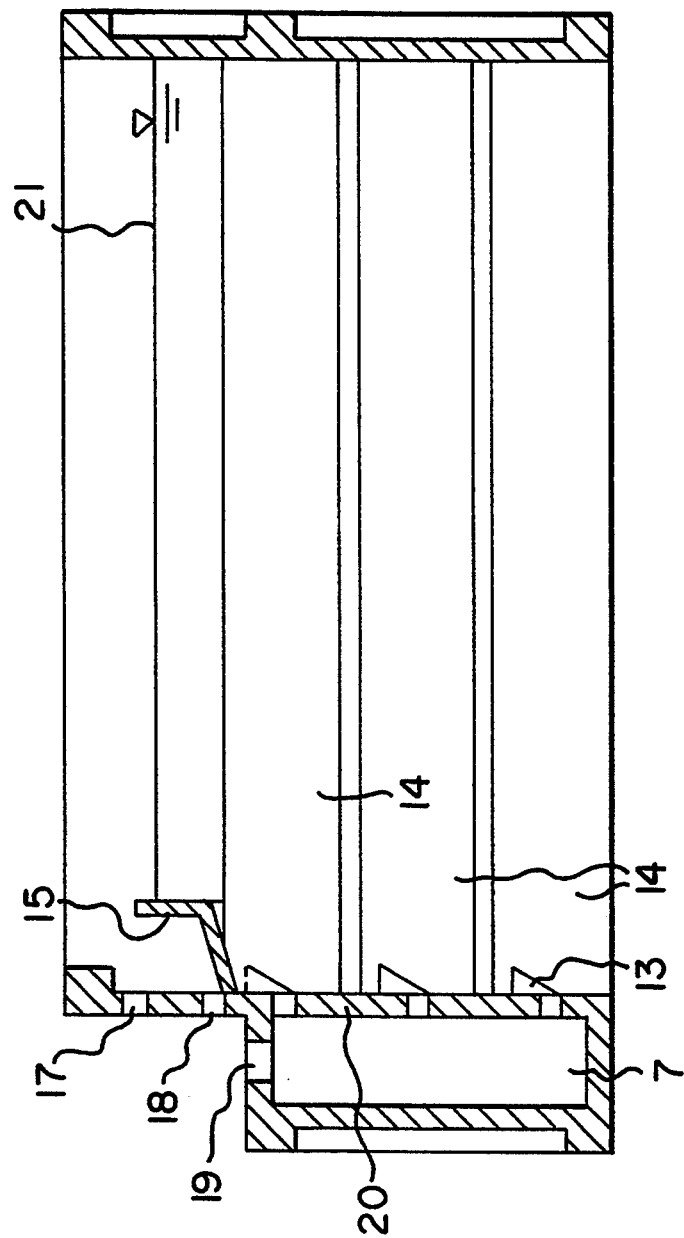
Figure 5:
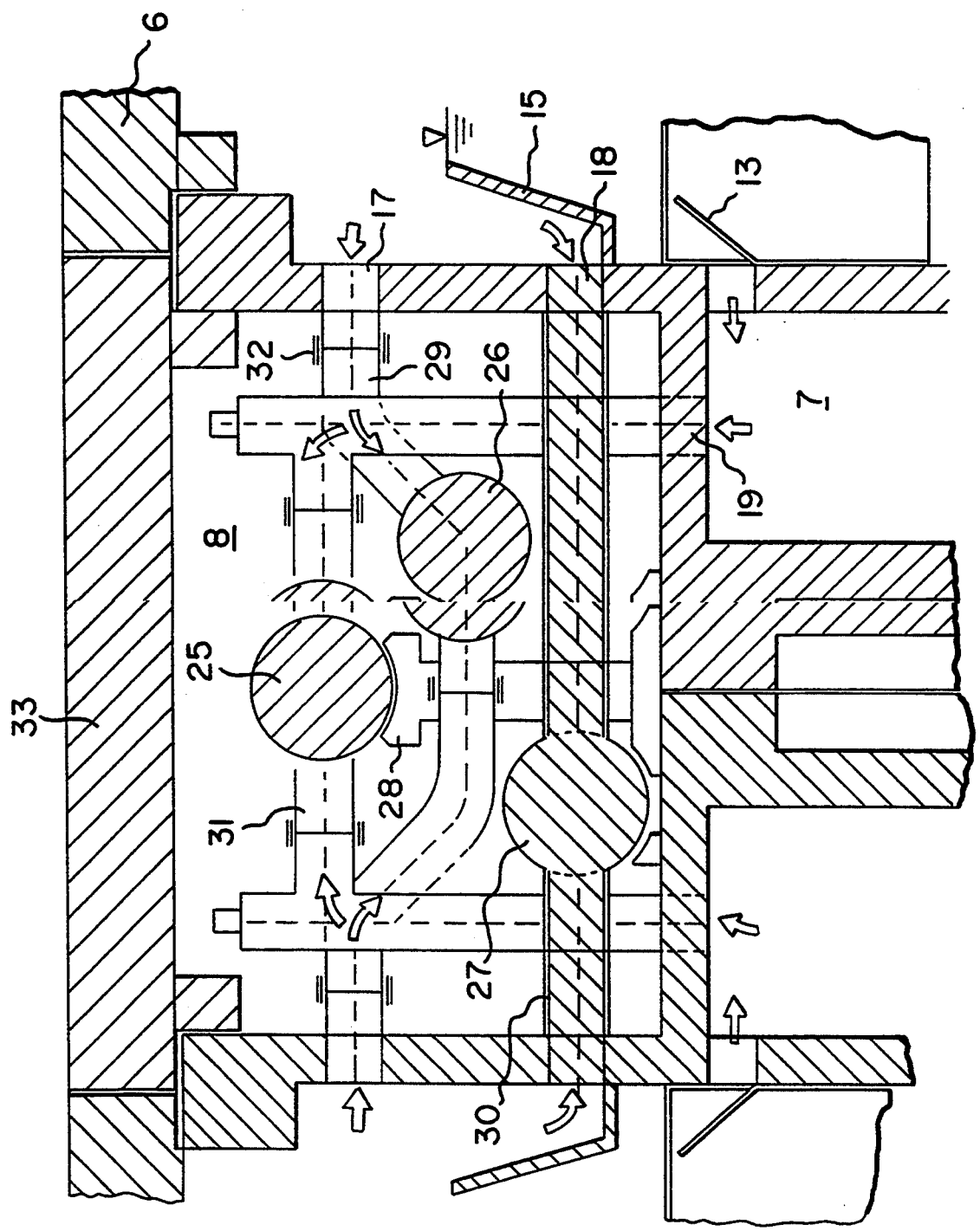

Other preferred construction characteristics are found in the description of an embodiment which is shown in the drawings:

FIG. 1 shows the horizontal projection of a section of an anaerobic reactor, equipped with four modules, FIG. 2 shows a vertical longitudinal section through a module according to FIG. 1, FIG. 3 shows an angled horizontal projection of the opened top of a module according to FIG. 1 which has been drawn in perspective, FIG. 4 shows a vertical cross-section through the module according to FIG. 1, FIG. 5 shows a cross-section through the discharge duct that is bordered by two modules.

In the horizontal projection according to FIG. 1, the exterior wall of the reactor is designated with 1. Dividing walls 2 and 3 represent the divisions for the central discharge compartment 4 and the adjacent section 5. Each module is covered by three covers 6. It is also shown that the modules, at their long sides, have projections 7. The projections 7 of the opposing modules abut each other and form the discharge duct 8 above them.

FIG. 2 shows the construction of a module. The side walls 10 consists of reinforcement profiles 11 that are covered completely with the plastic used as wall material. At the top, there are two cross-bars 12 which function as a sealing support for the covers 6. The visible long wall has a number of drain holes for the digester gas which are covered by pockets. The drain holes are located in the apex of gas collection domes 14 which here have a semi-circular cross-section. The collection domes overlap each other so that no digester gas can escape into the atmosphere.

The clear water overflow channel 15 which here has a toothed inlet edge is located above the top layer of the collection domes.

FIG. 3 shows that drains for waste air 17 and clear water 18 are located in the wall section 16 above the projecting section 8. The digester gas collected in the projecting section 8 is evacuated upwards through openings 19. This is also shown in FIG. 4. The projecting section 8 is separated from the module interior by a dividing wall 20. The clear water overflow channel 15 determines the water level 21 in the reactor.

FIG. 5 shows two modules which abut each other in a sealing manner with their projecting sections 7. The two projecting sections 7 form a free discharge duct 8 above them that holds the three conduit pipes for removing digester gas 25, waste air 26, and clear water 27. Two of the conduit pipes rest on consoles 28 so that they can be removed in sections in order to access the pipe duct beneath them. The connecting pipes 29, 30, 31 are connected via socket-less pipe clamps 32, whereby the digester gas pipe connection which is passed around the waste air collection pipe 26 is constructed as a T-pipe with a top connection for probes for measuring volume and noxious substances. Special covers 33 are provided for the discharge duct 8.

The discharge duct 8 merges into a main channel 34 (FIG. 1) that also contains feed lines 35 for the waste water to be treated.

We claim:

1. An UASB reactor for anaerobic waste water treatment comprising:
   a plurality of modules, each module comprising:
      walls defining the module, an overflow channel for treated waste water, the height of said overflow channel defining an overflow threshold, a plurality of immersed collection domes for collecting digester gas, said domes being staggered over an entire cross-section of the module and each including a gas drain which drains into a collection pipe, said collection pipe feeding into a top evacuation line, an air drain which drains into a middle evacuation line for collecting waste air above the water level of said overflow channel, a water drain which drains into a lower evacuation line for removing water from said overflow channel, said gas drain, said air drain, and said water drain all located on a common side of the module and being connected in a gas tight manner with said top evacuation line, said middle evacuation line and said lower evacuation line, respectively, and means for covering the module; and a discharge duct external to all of said modules, said discharge duct including said top evacuation line, said middle evacuation line, and said lower evacuation line, and means for closing off said evacuation lines in said discharge duct from communication with the drains on each of said modules.

2. Reactor according to claim 1 wherein each module further comprises a projecting compartment for the collection of digester gas at said common side and extending over the entire depth of the module and wherein said discharge duct runs along the top of said projecting compartment.

3. Reactor according to claim 1, said evacuation lines in said discharge duct being continuous and equipped with releasable and lockable connection pieces to the drains.

4. Reactor according to claim 3, releasable connections between said connection pieces and said evacuation lines being constructed as socket-less pipe clamps.

5. Reactor according to claim 2, said evacuation lines being supported on the projecting compartments by consoles.

6. Reactor according to claim 1, said collection domes comprising plastic pipes which have been split in half longitudinally.

7. Reactor according to claim 6, further comprising gluing/welding means for connecting said collection domes with the front walls of the modules.

8. Reactor according to claim 1, further comprising:
means for covering said discharge duct; and
all of said walls, said module covering means, said discharge duct covering means, said domes, said overflow channel, and said collection pipe being plastic.

9. Reactor according claim 8 further comprising steel profiles reinforcing said plastic.

* * * * *